United States Patent [19]

Sehring et al.

[11] 4,150,124
[45] Apr. 17, 1979

[54] 2,5-DICHLORO-4-CYANO-PHENYL ESTERS OF THIONOPHOSPHORIC, THIONOTHIOLPHOSPHORIC AND THIONOPHOSPHONIC ACIDS

[75] Inventors: Richard Sehring, Ingelheim am Rhein; Ricarda Prokic-Immel, Mainz, both of Fed. Rep. of Germany

[73] Assignee: Celamerck Gmbh & Co., KG Ingelheim am Rhein, Fed. Rep. of Germany

[21] Appl. No.: 824,414

[22] Filed: Aug. 15, 1977

Related U.S. Application Data

[63] Continuation of Ser. No. 764,809, Feb. 2, 1977, abandoned.

[30] Foreign Application Priority Data

Feb. 21, 1976 [DE] Fed. Rep. of Germany ....... 2607176

[51] Int. Cl.² ........................ A01N 9/36; C07F 9/165; C07F 9/40
[52] U.S. Cl. .................................... 424/210; 260/940
[58] Field of Search ......................... 260/940; 424/210

[56] References Cited

U.S. PATENT DOCUMENTS 3,250,826  5/1966  Tamurs, et al. ..................... 260/940
3,839,511  10/1974  Kishino, et al. ................. 260/940 X

*Primary Examiner*—Anton H. Sutto
*Attorney, Agent, or Firm*—Hammond & Littell

[57] ABSTRACT

Compounds of the formula

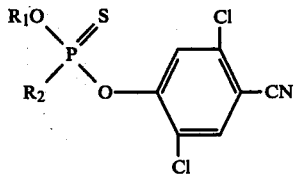

wherein
 $R_1$ is alkyl of 1 to 3 carbon atoms, and
 $R_2$ is alkyl of 1 to 3 carbon atoms, phenyl, alkoxy of 1 to 3 carbon atoms or (alkyl of 1 to 4 carbon atoms)thio;

the compounds are useful as insecticides, acaricides and fungicides.

9 Claims, No Drawings

2,5-DICHLORO-4-CYANO-PHENYL ESTERS OF THIONOPHOSPHORIC, THIONOTHIOLPHOSPHORIC AND THIONOPHOSPHONIC ACIDS

This is a continuation, of Ser. No. 764,809, filed Feb. 2, 1977, now abandoned.

This invention relates to novel 2,5-dichloro-4-cyano-phenyl esters of thionophosphoric, and thionothiolphosphoric and thionophosphonic acids, as well as to a method of preparing these compounds.

More particularly, the present invention relates to a novel class of phosphorus compounds represented by the formula

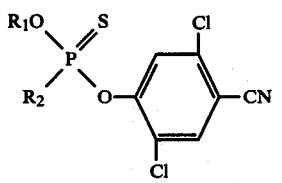

wherein
$R_1$ is alkyl of 1 to 3 carbon atoms, and
$R_2$ is alkyl of 1 to 3 carbon atoms, phenyl, alkoxy of 1 to 3 carbon atoms or (alkyl of 1 to 4 carbon atoms)thio.

Particularly preferred are those compounds of the formula I where the alkyl, alkoxy and alkylthio substituents contain from 1 to 2 carbon atoms.

The compounds embraced by formula I may be prepared by reacting a thionophosphoric, thionothiolphosphoric or thionophosphonic acid chloride of the formula

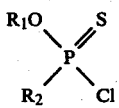

wherein $R_1$ and $R_2$ have the same meanings as in formula I, with 2,5-dichloro-4-cyano-phenol in the presence of an acid-binding agent or with a 2,5-dichloro-4-cyano-phenolate.

The reaction may be carried out in an organic solvent, such as toluene, dioxane, tetrahydrofuran or methylethyl ketone, or also in water at a temperature between about 30° and 90° C.

The phenolate reactant may be derived from an alkali metal base or from an organic base, such as triethylamine, ethylpiperidine, trimethylamine or the like.

For purification purposes, the raw reaction product is taken up in a suitable organic solvent, such as 1,2-dichloro-ethane, and the solution is washed with dilute sodium hydroxide and water, dried, treated with activated charcoal if required, and evaporated.

After the indicated purification procedure, the reaction product remains behind as a colorless to light yellow oil of sufficient purity. Some of the esters of the formula I are crystalline. In general, the compounds of the present invention can be distilled in a high vacuum without discernable decomposition.

The starting compounds of the formula II are either known compounds or may be prepared by known methods.

The following examples illustrate the present invention and will enable others skilled in the art to understand it more completely. It should be understood, however, that the invention is not limited solely to the particular examples given below.

EXAMPLE 1

O,O-Diethyl-O-(2,5-dichloro-4-cyano-phenyl)-thionophosphate 18.8 gm of 2,5-dichloro-4-cyano-phenol were dissolved in 100 ml of tetrahydrofuran, and the solution was admixed with 14.0 gm of potassium carbonate, whereby the potassium salt of the phenol was formed. While stirring, gm of O,O-diethyl-thionophosphoric acid chloride were slowly added dropwise at 50° to 60° C., and the resulting mixture was refluxed on a water bath for 3 hours. Thereafter, the reaction solution was filtered and evaporated. The residue was dissolved in 1,2-dichloro-ethane, and the solution was extracted with dilute sodium hydroxide. After drying of the dichloroethane phase with sodium sulfate, it was filtered, and the solvent was completely removed in vacuo from the filtrate, yielding 33.5 gm (98.5% of theory) of the compound of the formula

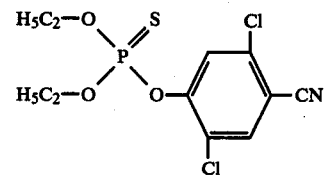

which was thin-layer-chromatographically uniform. After purification with a mixture of cyclohexane and methanol, the product was obtained in crystalline form having a melting point of 58° C.

EXAMPLE 2

Using a procedure analogous to that described in Example 1, 82% of theory of O,O-dimethyl-O-(2,5-dichloro-4-cyano-phenyl)-thionophosphate, refractive index: $n_D^{24}$ 1.6032, was obtained from potassium 2,5-dichloro-4-cyano-phenolate and O,O-dimethyl-thionophosphoric acid chloride.

EXAMPLE 3

Using a procedure analogous to that described in Example 1, 81% of theory of O,O-di-n-propyl-O-(2,5-dichloro-4-cyano-phenyl)-thionophosphate, refractive index: $n_D^{22}$ 1.5834, was obtained from potassium 2,5-dichloro-4-cyanophenolate and O,O-di-n-propyl-thionophosphoric acid chloride.

EXAMPLE 4

Using a procedure analogous to that described in Example 1, 74% of theory of O-ethyl-O-(2,5-dichloro-4-cyano-phenyl)-ethylthionophosphonate, refractive index: $n_D^{24}$ 1.5983, of the formula

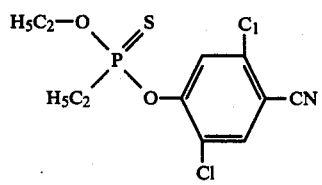

was obtained from potassium 2,5-dichloro-4-cyanophenolate and O-ethyl-ethylthionophosphonic acid chloride.

EXAMPLE 5

Using a procedure analogous to that described in Example 1, 78% of theory of O-isopropyl-O-(2,5-dichloro-4-cyano-phenyl)-methylthionophosphonate, refractive index: $n_D^{22}$ 1.6023, was obtained from potassium 2,5-dichloro-4-cyano-phenolate and O-isopropyl-methylthionophosphonic acid chloride.

EXAMPLE 6

Using a procedure analogous to that described in Example 1, 87% of theory of O-ethyl-O-(2,5-dichloro-4-cyano-phenyl)-phenylthionophosphonate, refractive index: $n_D^{23}$ 1.5221, was obtained from potassium 2,5-dichloro-4-cyano-phenolate and O-ethyl-phenylthionophosphonic acid chloride.

EXAMPLE 7

Using a procedure analogous to that described in Example 1, 78% of theory of O-ethyl-S-n-propyl-O-(2,5-dichloro-4-cyano-phenyl)-thionothiolphosphate, refractive index: $n_D^{25}$ 1.5703, of the formula

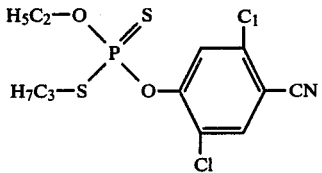

was obtained from potassium 2,5-dichloro-4-cyano-phenolate and O-ethyl-S-n-propyl-thionothiolphosphoric acid chloride.

EXAMPLE 8

Using a procedure analogous to that described in Example 1, O,S-dimethyl-O-(2,5-dichloro-4-cyano-phenyl)-thionothiolphosphate was obtained from potassium 2,5-dichloro-4-cyano-phenolate and O,S-dimethyl-thionothiolphosphoric acid chloride.

EXAMPLE 9

Using a procedure analogous to that described in Example 1, O,S-diethyl-O-(2,5-dichloro-4-cyano-phenyl)-thionothiolphosphate was obtained from potassium 2,5-dichloro-4-cyano-phenolate and O,S-diethyl-thionothiolphosphoric acid chloride.

EXAMPLE 10

Using a procedure analogous to that described in Example 1, O,S-diisopropyl-O-(2,5-dichloro-4-cyano-phenyl)-thionothiolphosphate was obtained from potassium 2,5-dichloro-4-cyano-phenolate and O,S-diisopropyl-thionothiolphosphoric acid chloride.

EXAMPLE 11

Using a procedure analogous to that described in Example 1, O-ethyl-S-isopropyl-O-(2,5-dichloro-4-cyano-phenyl-thionothiolphosphate was obtained from potassium 2,5-dichloro-4-cyano-phenolate and O-ethyl-S-isopropyl-thionothiolphosphoric acid chloride.

EXAMPLE 12

Using a procedure analogous to that described in Example 1, O-ethyl-O-S-n-butyl-O-(2,5-dichloro-4-cyano-phenyl)-thionothiolphosphate was obtained from potassium 2,5-dichloro-4-cyano-phenolate and O-ethyl-S-n-butyl-thionothiolphosphoric acid chloride.

EXAMPLE 13

Using a procedure analogous to that described in Example 1, O-ethyl-S-tert.butyl-O-(2,5-dichloro-4-cyano-phenyl)-thionothiolphosphate was obtained from potassium 2,5-dichloro-4-cyano-phenolate and O-ethyl-S-tert.butyl-thionothiolphosphoric acid chloride.

The compounds of the present invention, that is, those embraced by formula I above, have useful properties. More particularly, they exhibit insecticidal, acaricidal and fungicidal activities against oriental roaches, resistant aphids and genuine mildew, for example.

The insecticidal efficacy of O,O-diethyl-O-(2,5-dichloro-4-cyano-phenyl)-thionophosphate (A), for instance, was compared with that of the commercial product O,O-diethyl-O-(2,5-dichloro-4-bromo-phenyl)-thionophosphate (B) against oriental roaches. The following table shows the percent kill after two days at various concentrations.

| Compound | % kill after 2 days at active ingredient concentration | | |
|---|---|---|---|
|  | 0.6 ppm | 1.0 ppm | 2.5 pm |
| Invention: |  |  |  |
| A | 60 | 90 | 100 |
| Prior Art: |  |  |  |
| B | 0 | 10 | 30 |

For insecticidal, acaricidal or fungicidal application purposes the compounds of the present invention are incorporated as active ingredients into conventional pesticidal compositions consisting essentially of an inert carrier and an effective amount of the active ingredient, such as solutions, emulsions, suspensions, dusting powders or the like. The effective concentration of the compounds of this invention in such compositions is between about 0.01 and 5% by weight based on the total weight of the composition. However, the compounds of the formula I may also be incorporated as active ingredients into so-called ultra-low-volume (ULV) compositions which may contain up to about 90% by weight of active ingredient.

The following examples illustrate a few pesticidal compositions comprising a compound of the present invention as an active ingredient and represent the best modes contemplated of putting the invention into practical use.

EXAMPLE 14

Emulsion concentrate 20 parts by weight of O,S-diethyl-O-(2,5-dichloro-4-cyano-phenyl)-thionothiolphosphate were dissolved in 75 parts by weight of xylene, and the solution was admixed with 5 parts by weight of nonylphenol polyglycol ether. The resulting concentrate was, prior to use, emulsified in a sufficient amount of water to make the active ingredient concentration in the aqueous emulsion between 0.01 and 0.1% by weight based on the total weight.

EXAMPLE 15

Dusting powder 2 parts by weight of O,O-diethyl-O-(2,5-dichloro-4-cyano-phenyl)-thionophosphate were sprayed onto 98 parts by weight of kaolin, and the mixture was milled into a homogeneous powder.

EXAMPLE 16

Wettable powder 25 parts by weight of O-ethyl-O-(2,5-dichloro-4-cyano-phenyl)-ethylthionophosphonate were sprayed onto 73 parts by weight of diatomaceous earth, 2 parts of sodium naphthalene sulfonate were added, and the resulting mixture was milled into a homogeneous powder. Prior to use, the powder was admixed with a sufficient amount of water to make the active ingredient concentration of the aqueous suspension between 0.01 and 0.1% by weight based on the total weight.

Any one of the other compounds embraced by formula I may be substituted for the particular active ingredient in Examples 14 through 16. Likewise, the amount of active ingredient in these illustrative examples may be varied to achieve the effective concentration range set forth above, and the amounts and nature of the inert carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

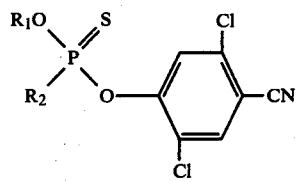

wherein
  $R_1$ is alkyl of 1 to 3 carbon atoms, and
  $R_2$ is alkyl of 1 to 3 carbon atoms, phenyl, alkoxy of 1 to 3 carbon atoms or (alkyl of 1 to 4 carbon atoms)thio.

2. The method of killing insects, acarids or fungi, which comprises contacting the same with an effective insecticidal, acaricidal or fungicidal amount of a compound of claim 1.

3. A compound of claim 1,
where
  $R_1$ is alkyl of 1 to 2 carbon atoms, and
  $R_2$ is alkyl of 1 to 2 carbon atoms, phenyl, alkoxy of 1 to 2 carbon atoms or (alkyl of 1 to 2 carbon atoms)thio.

4. The compound of claim 3 which is O,O-diethyl-O-(2,5-dichloro-4-cyano-phenyl)-thionophosphate.

5. The compound of claim 3 which is O,O-dimethyl-O-(2,5-dichloro-4-cyano-phenyl)-thionophosphate.

6. The compound of claim 3 which is O-ethyl-O-(2,5-dichloro-4-cyano-phenyl)-ethylthionophosphonate.

7. The compound of claim 3 which is O,S-dimethyl-O-(2,5-dichloro-4-cyano-phenyl)-thionothiolphosphate.

8. The compound of claim 3 which is O,S-diethyl-O-(2,5-dichloro-4-cyano-phenyl)-thionothiolphosphate.

9. A pesticidal composition consisting essentially of an inert carrier and an effective insecticidal acaricidal or fungicidal amount of a compound of claim 1.

* * * * *